(12) United States Patent
Steinseifer et al.

(10) Patent No.: US 10,001,129 B2
(45) Date of Patent: Jun. 19, 2018

(54) IMPELLER OF A CENTRIFUGAL PUMP APPARATUS

(71) Applicant: Reinheart GmbH, Bad Oeynhausen (DE)

(72) Inventors: Ulrich Steinseifer, Hauset (BE); Fiete Boehning, Aachen (DE); Thomas Schmitz-Rode, Aachen (DE)

(73) Assignee: REINHEART GMBH, Bad Oeynhausen (DE)

( * ) Notice: Subject to any disclaimer, the term of this patent is extended or adjusted under 35 U.S.C. 154(b) by 139 days.

(21) Appl. No.: 14/779,208

(22) PCT Filed: May 23, 2013

(86) PCT No.: PCT/EP2013/001516
§ 371 (c)(1),
(2) Date: Sep. 22, 2015

(87) PCT Pub. No.: WO2014/187466
PCT Pub. Date: Nov. 27, 2014

(65) Prior Publication Data
US 2016/0061209 A1    Mar. 3, 2016

(51) Int. Cl.
*F04D 29/04* (2006.01)
*F04D 29/047* (2006.01)
(Continued)

(52) U.S. Cl.
CPC ....... *F04D 29/0473* (2013.01); *A61M 1/1017* (2014.02); *F04D 13/026* (2013.01);
(Continued)

(58) Field of Classification Search
CPC .. F04D 29/0473; F04D 29/0413; F04D 29/22; F04D 13/026; F04D 13/024;
(Continued)

(56) References Cited

U.S. PATENT DOCUMENTS 2,899,243 A * 8/1959 Acterman ............... F16C 17/08
384/121
4,348,065 A * 9/1982 Yoshioka ................ F16C 17/04
384/121
(Continued)

FOREIGN PATENT DOCUMENTS

JP    2005270415 B    10/2005
WO   2006/137496 A1   12/2006
(Continued)

*Primary Examiner* — Devon Kramer
*Assistant Examiner* — Christopher Bobish
(74) *Attorney, Agent, or Firm* — Andrew Wilford

(57) ABSTRACT

The invention relates to an impeller (1) of a centrifugal pump apparatus, in particular of a blood pump apparatus, comprising a discoidal body (1) rotatable around an axis (2) of rotation, the body (1) comprising an upper surface (3), a lower surface (4), a central channel (5) extending in the direction of the axis (2) of rotation between the upper and lower surface (3, 4) for guiding fluid, in particular blood through the body (1) in axial direction when the body (1) is rotated in a pump chamber of a pump and several blades (6) supported by the upper surface (3) for pumping fluid, in particular blood, when the body (1) is rotated in a pump chamber of a pump, several spiral grooves (7) in the lower surface (4), each groove (7) having a bottom (7a) and two sidewalls (7b, 7c) and being open in an axial direction, merging into a circumferential surface (8) of the body (1) and extending from this circumferential surface (8) to the central channel (5) at least for providing a pumping action of fluid, in particular blood, from the circumferential surface (8) to the central channel (5) when the body (1) is rotated within a pump chamber of a pump, permanent magnets (10) integrated in the body (1) for driving the impeller by means of a magnetic field wherein each groove (7) is also merging into the central channel (5), one of the sidewalls (7b) of each groove (7) being higher above the bottom (7a) than the other (Continued)

sidewall (7c), in particular the leading sidewall (7b) with respect to the regular direction (R) of rotation being higher than the trailing sidewall (7c), a respective surface area (9) being disposed between each two neighboring grooves (7) and connecting the leading sidewall and the trailing sidewall of neighboring grooves, in particular thus forming a tilted pad area between each pair of neighboring grooves. The invention furthermore relates to a centrifugal blood pump apparatus comprising such an impeller.

11 Claims, 2 Drawing Sheets

(51) Int. Cl.
| | | |
|---|---|---|
| *F04D 29/041* | (2006.01) | |
| *F04D 29/22* | (2006.01) | |
| F04D 13/02 | (2006.01) | |
| F04D 13/06 | (2006.01) | |
| A61M 1/10 | (2006.01) | |
| A61M 1/12 | (2006.01) | |
| F04D 1/00 | (2006.01) | |

(52) U.S. Cl.
CPC ......... *F04D 29/0413* (2013.01); *F04D 29/22* (2013.01); *A61M 1/101* (2013.01); *A61M 1/1031* (2014.02); *A61M 1/122* (2014.02); *F04D 1/00* (2013.01); *F04D 13/024* (2013.01); *F04D 13/0646* (2013.01)

(58) Field of Classification Search
CPC ............. F04D 13/0646; F04D 29/1513; F04D 29/057; F04D 29/2266; F04D 29/047; F04D 1/00; A61M 1/1017; A61M 1/1031; A61M 1/1036; A61M 1/101; A61M 1/122
See application file for complete search history.

(56) References Cited

U.S. PATENT DOCUMENTS

| | | | | |
|---|---|---|---|---|
| 5,829,338 | A | * | 11/1998 | Chrestoff ............... F04B 1/148 384/121 |
| 5,947,703 | A | * | 9/1999 | Nojiri ................... A61M 1/101 415/229 |
| 6,036,435 | A | * | 3/2000 | Oklejas ................. F16C 33/102 415/106 |
| 6,089,754 | A | * | 7/2000 | Wilkes ..................... F16C 17/06 384/122 |
| 6,132,094 | A | * | 10/2000 | Cornelison ............. F16C 17/04 384/121 |
| 6,227,797 | B1 | | 5/2001 | Watterson et al. |
| 6,227,817 | B1 | | 5/2001 | Paden |
| 6,976,788 | B2 | * | 12/2005 | Honda ................ F16C 33/1065 384/123 |
| 7,128,538 | B2 | | 10/2006 | Tsubouchi |
| 7,470,064 | B2 | * | 12/2008 | Link ..................... F01D 25/168 384/121 |
| 7,748,964 | B2 | | 6/2010 | Taegashi et al. |
| 7,832,934 | B2 | * | 11/2010 | Hemmi ................... F16C 17/04 384/121 |
| 8,540,477 | B2 | * | 9/2013 | LaRose ................. A61M 1/101 415/106 |
| 8,672,611 | B2 | * | 3/2014 | LaRose ................. A61M 1/101 415/104 |
| 9,133,854 | B2 | | 9/2015 | Takehisa |
| 9,227,001 | B2 | * | 1/2016 | Akkerman ............ A61M 1/101 |
| 9,242,032 | B2 | * | 1/2016 | LaRose ................. A61M 1/101 |
| 9,382,908 | B2 | * | 7/2016 | Ozaki ................... A61M 1/101 |
| 2011/0238172 | A1 | * | 9/2011 | Akdis ................... A61M 1/101 623/3.11 |

FOREIGN PATENT DOCUMENTS

| | | |
|---|---|---|
| WO | 2010029296 A | 3/2010 |
| WO | 2014000753 A | 1/2014 |

\* cited by examiner

IMPELLER OF A CENTRIFUGAL PUMP APPARATUS

CROSS REFERENCE TO RELATED APPLICATIONS

This application is the US-national stage of PCT application PCT/EP2013/001516 filed 23 May 2013 and claiming the priority of PCT patent application PCT/EP2013/001516 itself filed 23 May 2013.

FIELD OF THE INVENTION

The invention relates to an impeller of a centrifugal pump.

BACKGROUND OF THE INVENTION

In such a blood pump, the impeller comprising a discoidal body rotatable around an axis of rotation, the body comprising an upper surface, a lower surface and a central passage extending in the direction of the axis of rotation between the upper and lower surface for guiding fluid, in particular blood through the body in axial direction when the body is rotated in a pump chamber of a pump and comprising several blades supported by the upper surface for pumping fluid, in particular blood, when the body is rotated in a pump chamber of a pump and several spiral grooves in the lower surface, each groove having a bottom and two sidewalls and being open in an axial direction, merging into an outer surface of the body and extending from this outer surface to the central passage at least for providing a pumping action of fluid, in particular blood, from the outer surface to the central passage when the body is rotated within a pump chamber of a pump and permanent magnets integrated in the body for driving the impeller by a magnetic field, the magnetic field being generatable by a magnetic drive, for example an electro-magnetic drive positioned on the outside of a pump housing and arranged around the axis of rotation.

The present invention furthermore relates to rotary pumps and, more specifically, to centrifugal rotary blood pumps utilizing hydrodynamic or a combination of hydrodynamic and magnetic bearings for contactless suspension and rotation of such an impeller. This allows wearless pump operation and thus prolonged lifespan.

Mechanical circulatory support with left ventricular assist devices (LVADs) to treat end-stage heart failure has broadly demonstrated beneficial outcomes. For long-term applications, such as destination therapy or prolonged bridge to transplant, fully implantable ventricular assist devices are most suited.

Rotary blood pumps, including centrifugal, axial and mixed flow pumps, have the advantage in their small size while being able to achieve full cardiac support, particularly the newest, 3rd generation devices which are rotary pumps with non-contact suspension of the impeller.

Centrifugal pumps have their optimal hydraulic efficiency at lower rotational speeds than axial or mixed flow pumps. The non-contact suspension techniques, passive and active magnetic as well as hydrodynamic, have each certain advantages and limitations that need to be addressed. Passive magnetic bearings can generate high forces to allow operation at high clearance gaps with lowest implied energy losses; they are also less complicated compared to active magnetic bearings.

However, a full passive magnetic bearing is physically not achievable in blood pumps and hence needs to be combined with a second, different suspension type. Active magnetic bearings can also operate at high clearance gaps but need a sophisticated control and feedback system because of their intrinsic instability, what can result in high energy consumption. Furthermore active magnetic bearings may have the problem of failure of electronic components and/or drift of sensors. They also require additional space for the bearing system components, including electronics, coils and sensors.

Hydrodynamic bearings on the other hand are completely passive and do not require active controllers. They do imply energy consumption, mainly due to the induced viscous flow losses. In principle, they incorporate small clearance gaps to create the pressure build-up, which yields the suspension force on the impeller.

These small clearance gaps however increase the flow resistance and thus reduce the bearing wash out flow. Sufficient and continuous fluid flow paths through the bearing sections are crucial though for the wash out. They can reduce the risk of hemolysis and thrombosis of the blood by reducing the exposure time of the fluid to areas of high shear stress as well as avoiding regions of low flow or flow stagnation.

Hence, by developing more sophisticated bearing designs for impellers in rotary blood pumps that combine sufficient load and momentum capacity with sufficient and continuous wash out flow through the bearing section, the reliability and safety of consistent therapeutic support with rotary blood pumps shall be improved.

The patent application PCT/EP 2012/002722 of the same applicant discloses a centrifugal blood pump comprising a housing having an inlet port, an outlet port and a pump chamber connecting these ports and an impeller located in the pump chamber and rotatable around an axis of rotation being coaxial with the inlet port, the impeller having a central axial opening/passage, communicating with the inlet port, several blades and free spaces between the blades, in particular the free spaces being radially open and communicating with the central axial opening and with the outlet port via a volute surrounding the impeller and a magnetic drive, driving the impeller by a magnetic field interacting with permanent magnets integrated in the impeller and a hydrodynamic bearing by several spiral grooves in a lower surface of the impeller opposite to a mating inner surface of a lower wall of the pump chamber. This pump furthermore uses an impeller of the above-mention kind for propelling blood.

During operation the rotating blades or vanes supported on the upper surface of the impeller are pumping blood from the inlet port through the inner central opening or passage of the impeller body to the outlet port. Besides this first blood flow path a secondary internal flow path exists due to the spiral grooves in the lower surface of the impeller body and the gap between this lower surface and a pump housing that exist during rotation. These grooves are pumping blood from the upper surface via the outer surface of the impeller body to the central passage/opening along the lower surface.

By means of the fact that the grooves of this known impeller body extend from the outer surface to the central passage/opening but end prior to the central opening a rising blood pressure is established near the central opening between the lower surface and a opposed wall of the pump chamber that provides a hydrodynamic contactless suspension of the impeller without any mechanical bearings.

Additionally a contactless radial journal bearing may exist when the impeller is rotated for radial stabilization.

Even though this construction allows contactless suspension of the impeller and a washout effect of blood, there is not enough tilt restoration when accidental shock forces are exerted to the pump. As a consequence there is a risk of touchdown of the rotating impeller within the pump chamber/housing unless other electrical or magnetic tilt restoration mechanisms exist.

OBJECT OF THE INVENTION

It is an object of the present invention to improve such a known impeller and a pump, using such an impeller in order to still provide contactless hydrodynamic suspension and to provide better tilt restoration without or with less additional electrical and/or magnetic tilt restoration mechanisms.

SUMMARY OF THE INVENTION

This object is solved by the afore-mentioned impeller that is furthermore improved by the features that each groove is also merging into the central passage, one of the sidewalls of each groove being higher above the groove bottom than the other sidewall, in particular the leading sidewall with respect to the regular direction of rotation being higher than the trailing sidewall and a respective surface area being disposed between each two neighboring grooves and connecting the leading sidewall and the trailing sidewall of neighboring grooves.

By means of this surface area a tilted pad is established between each pair of neighboring grooves and the counter surface on the pump chamber. This yields a conjunction of the suspension capacity of tilted pad bearings with the high wash out of spiral groove bearings of the common kind.

The object is also solved by using such an impeller in a pump, in particular a centrifugal pump of pumping blood during heart assistance.

According to a preferred embodiment, each surface area may be subdivided into two parts in circumferential direction, a first part being adjacent to the higher sidewall of a groove forming a plateau in circumferential direction and a second part extending between the plateau and a neighboring groove (preceding groove) having a decreasing height toward the neighboring groove (preceding groove) in circumferential direction.

According to the invention, this construction at least exists at the outer radial position of the impeller body, preferably also in the area between the central passage and the outer surface.

The technical problem solved by this invention is the challenge of providing high load capacity for axial and tilt restoration of the impeller in a rotary blood pump while simultaneously providing sufficient wash-out of the bearing area. This washout is particularly of importance when the bearing area (area in which the hydrodynamic pressure is build up) is in a so called secondary flow path.

Furthermore, a high wash-out can be beneficial at surfaces of elevated temperatures as possible near the motor stator.

In rotary blood pumps, elevated temperatures, prolonged residence times of blood in the device and elevated shear stresses due to small clearances can cause complications like thrombus formation and hemolysis. A reduction of residence time and shear stresses as well as high heat dissipation, can thus lower the risk for the mentioned complications. A low residence time and high heat dissipation can be achieved by increased wash-out flow and a low shear stress can be achieved by large clearances which are determined strongly through the force and momentum capacity.

The invention is a design for a hydrodynamic chamfer bearing which due to its design provides optimal load capacity and high wash out. This is achieved by forming chamfer bearings with particularly designed grooves in a particular spiral shape such that upon rotation the fluid is pumped toward the center. The working principle of chamfer bearings is such that they create elevated pressures due to the relative motion of an inclined surface to a counter surface which together yield a narrowing clearance in the direction of the fluid flow through it.

The presented design of the invented chamfer bearing is particularly optimized for centrifugal rotary blood pumps in regards of geometrical features and dimensions, pressure conditions and fluid properties.

Typical geometrical features are the rotor vanes to pump the fluid as well as shrouds covering either the top or bottom side of the vanes, or both. In particular a further feature includes a somehow formed inner flow inlet area to the vanes, mostly cylindrical in shape and located between the inflow cannula and the rotor vanes.

Because of the fact that in newest rotary blood pumps the rotor is driven contact free and thus no shaft or mechanical bearings are present, so called secondary flow paths can be present. Typical geometrical dimensions for a centrifugal blood pump would include an outer impeller diameter of about 40 mm and an inner cylindrical inlet with a diameter of about 10 mm.

The particular design of the invented chamfer thrust bearing comprises a circumferentially repeating pattern of an inclined surface, a plateau area and a groove (a set of inclined surface and plateau is herein called pad). These structures are formed in a particularly formed spiral shape such that upon rotation, fluid is pumped toward the center of the impeller. The design is optimized for tilt restoration, axial force and wash-out.

Due to the fact, that grooves in the lower surface of the impeller body exist that totally extend between and merge into the outer surface and the central passage respectively, a higher washout can be realized compared to the construction in the known state of the art as described.

This surface area, in particular the tilted/inclined second part of it, provides a pressure build-up in order to establish the contactless suspension of the impeller. Compared to the known contactless suspension by grooves, only this construction furthermore moves the locations/area of high pressure from the central region surrounding the passage more to an outer radial position or preferably to an area being close to the outer surface. Accordingly tilt restoration is improved by higher tilt restoring torque due to the bigger distance of the restoring force to the central passage.

According to a preferred embodiment in circumferential direction, the first part of the surface area may form a plane plateau but it should be noted that also a curved, in particular a convex surface may be established in relation to an opposing surface, in particular of a pump housing wall.

Furthermore, in circumferential direction, the second part of the surface area may monotonically decrease in height, in particular in a straight line toward the neighboring groove, in particular a leading groove (in normal rotation) in particular until it merges into the lower sidewall of the neighboring groove.

According to a further improvement, in a direction from the outer surface toward the central passage of the impeller body, the free space between two neighboring grooves and between the lower surface and a counterpart surface, in particular a wall of a pump chamber, is decreasing. This corresponds to a narrowing gap existing between the impeller and a wall of the pump chamber in radial direction toward the central passage, thus providing an additional pressure build-up near the central passage may be realized.

Reducing the free space/narrowing the gap may be realized in different ways.

The grooves may comprise a decreasing cross-section toward the central passage particularly by an inclined (rising) bottom surface of the groove. Additionally, in direction toward the center passage, the groove width may be enlarged in size with relation to the regular width yielded by the spiral shape. That way manufacturing of these grooves can be significantly simplified. This embodiment of changing the bottom surface position of a groove may be combined with the following embodiments unless it is explicitly excluded.

In a possible embodiment, in a direction from the outer surface to the central passage, the height of the higher sidewall may be constant and the height of the lower sidewall may be increasing, in particular by simultaneously maintaining the bottoms of two neighboring grooves within the same plane, in particular thus providing a second part of the surface area between two grooves whose slope in circumferential direction is decreasing with decreasing distance to the central passage.

In another embodiment, in a direction from the outer surface to the central passage, the height of the higher sidewall and thus the height of the plateau may be increasing, in particular by simultaneously maintaining the bottoms of two neighboring grooves within the same plane or changing (rising) them as mentioned.

Furthermore this may be improved by the feature, that in a direction from the outer surface to the central passage, the height of the lower sidewall is increasing by the same gradient as the higher sidewall increases, particularly thus providing a second part of the surface area between two grooves that is increasing in height above the groove bottoms and maintaining its slope in circumferential direction constant.

According to another embodiment, in a direction from the outer surface to the central passage, the height of the lower sidewall may be increasing by a smaller gradient than the higher sidewall or may be constant, in particular thus providing a second part of the surface area between two grooves having a slope in circumferential direction that is increasing with decreasing distance to the central passage.

According to all these embodiment and possible other—non mentioned—embodiments, the mentioned surface area, in particular the first part (plateau) and/or the second part may form a secondary incline along a spiral line on the lower surface of the impeller body toward the rotor center.

A pump and impeller design for which the invented bearing design is particularly beneficial might comprise a center through hole and a secondary flow path at the bottom side of the impeller (between bottom shroud and casing) where possibly the motor stator is positioned, as know from the afore-mentioned state of the art of the same applicant.

This design allows for short distances of motor stator to rotor which is beneficial when a direct electromagnetic drive is used. In that case the wash-out of that area is even more important, because the surfaces could be prone to elevated temperatures.

The invention has a unique structure which utilizes specifically designed hydrodynamic thrust bearings (HTB) using a pattern of inclined surfaces, plateau areas and grooves, formed in a spiral shaped manner to improve restoring forces and moments, and wash-out of the bearing area. The details of the invention proposed in this patent application are summarized as below:

Hydrodynamic thrust bearing (HTB) which is designed for centrifugal rotary blood pumps to provide restoring axial forces and tilt moments HTB which is located within the secondary flow path HTB comprising inclined surfaces, plateau areas and grooves (a set of an inclined surface and a plateau is herein called pad)

HTB in which the above mentioned design is formed in a spiral shape toward the rotational center (orientation of the spiral shape in such a way that fluid is pumped toward the rotor center upon rotation)

HTB which, additionally to the force and moment creation, provides improved wash-out of the bearing area and thus of the secondary flow path HTB wherein the inclined surface can be secondarily inclined with respect to the radial or spiral shape direction HTB wherein the inclined surface yields an angle of less than 1° with the plane of the plateau surface HTB wherein the groove depth is preferably, but not restricted to, around 260 pm HTB wherein the groove can have a varying depth (for the purpose of reducing the groove cross-section toward the rotor center)

HTB wherein the groove can have a widened width (e.g. >0.5 mm) toward the rotor center for ease of manufacturing HTB with preferably 5 pads for a rotor of around 40 mm in diameter (for rotors with smaller diameter, less pads can be preferably, and vice versa)

According to the innovations above, this invented device has the advantages of high momentum restoration and axial restoring force and high (improved) washout of the bearing area.

SPECIFIC DESCRIPTION OF THE INVENTION

Figure 1:
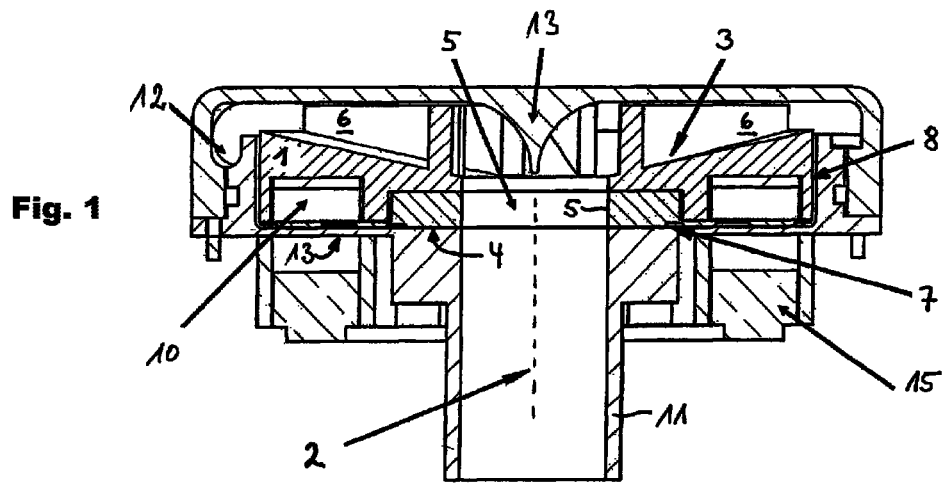
FIG. 1 shows a blood pump using an impeller 1 according to the invention.

A rotary blood pump is provided with a fully suspended impeller 1 having free spaces between the impeller blades 6 open axially and radially. An inlet port 11 is provided for blood entering the central passage 5 in the impeller 1, being redirected from an axial direction into a radial direction by the cone 13 projecting from the upper wall of the pump chamber into the central passage 5 and being discharged via a volute into the exit port 12 of the apparatus.

The impeller may be driven by an axially aligned motor (axial flux) which may create an adjustable force in the axial direction through the attractive force of the stator 15 and the rotor permanent magnets 10.

The impeller 1 is fully blood suspended by the inventive bearing construction having spiral grooves 7 and tilted pads in the lower surface 4 of the impeller 1 and in this case also by a radial journal bearing for which the impeller 1 is eccentrically positioned in the pump chamber.

A second flow path exists between the blades 6, the outer surface 8, the grooves 7 and the central passage 5 providing a washout of the suspending blood.

Figure 2:
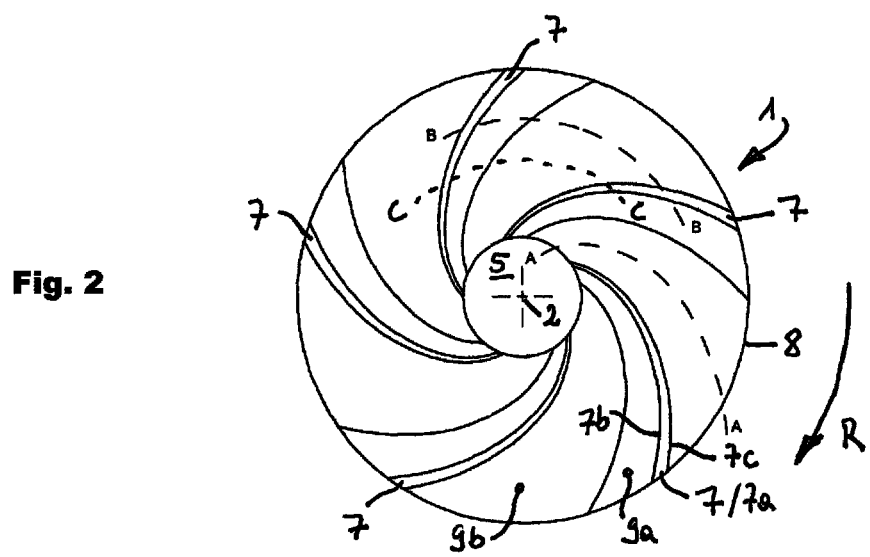
FIG. 2 is a top view on the lower surface 4 of the impeller 1.

FIG. 2 is a top view on the lower surface 4 of the impeller 1. Several grooves 7 exist that extend in a spiral shape between the outer surface 8 and the central passage 5. According to this embodiment each groove merges into the outer surface and the central passage 5.

Figure 3:
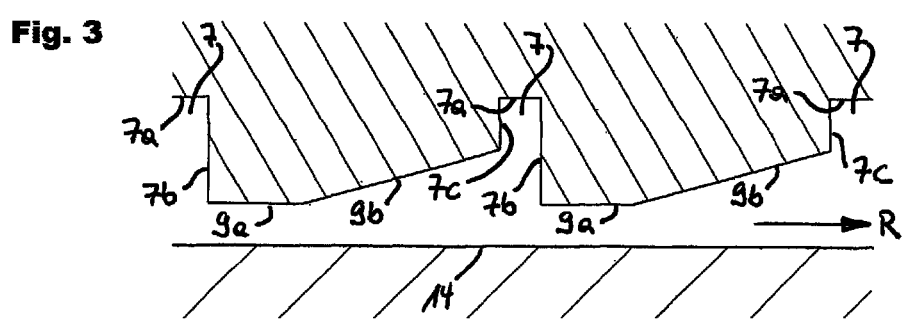
FIG. 3 is a section taken along line B-B of FIG. 2.

FIG. 3 shows a cross-sectional view along the section B-B of FIG. 2, i.e. a section at a constant radial distance to the axis of rotation 2. In relation to the normal direction of rotation R each groove 7 has a bottom 7a, a higher leading sidewall 7b and a lower trailing sidewall 7c. The trailing sidewall 7c of a groove 7 is connected to a leading sidewall 7b of the neighboring groove 7 by a surface area 9 that is at least partially inclined and acts as so-called pad.

In this specific embodiment the surface area 9 is subdivided into a first part 9a forming a plateau, in particular a plane plateau and a second part 9b whose height (above the groove bottom) is descending from the plateau to the trailing sidewall 7c of the other groove 7.

Figure 4:
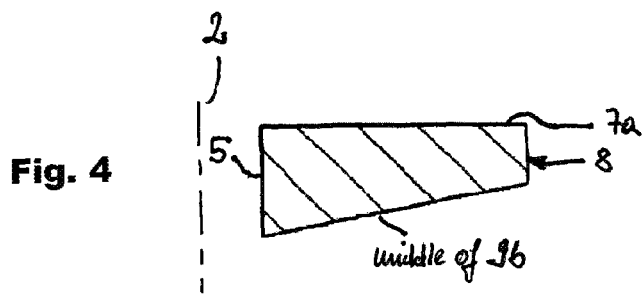
FIG. 4 is a section taken along line A-A of FIG. 2.

FIG. 4 depicts that along the section A-A, which is here i.e. the middle of the second part 9b, the free space between two neighboring grooves and a wall 14 of a pump housing is decreasing toward the central passage 5. At least the second part 9b of the surface area 9 has a rising height above the groove bottom 7a in this direction to provide this.

Figure 5:
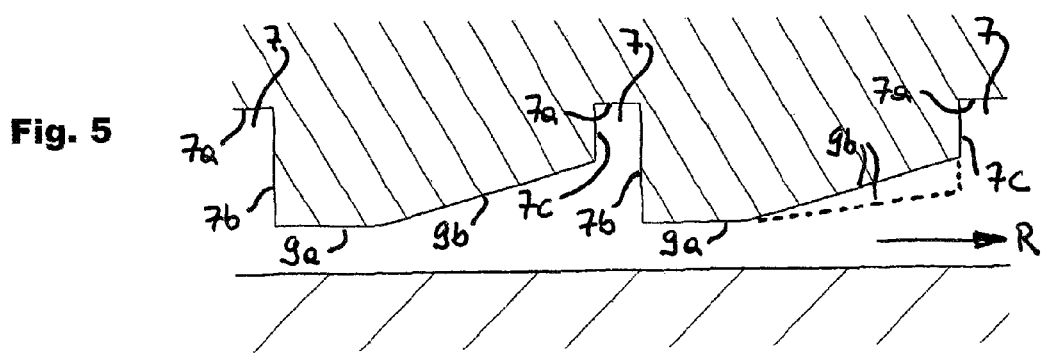
FIG. 5 is a section taken along line C-C of FIG. 2.

FIG. 5 shows a comparison of the surface area 9 in circumferential direction at two different radial positions, i.e. at section B-B, as discussed in FIG. 3 and at C-C, a section at a smaller radius value than section B-B. It can be seen here that at section C-C according to the dashed line the slope of the second part 9b decreases toward the central passage and its height rises by an also rising height of the trailing sidewall 7c of the groove 7 in the same direction. This is in accordance with FIG. 4.

Figure 6:
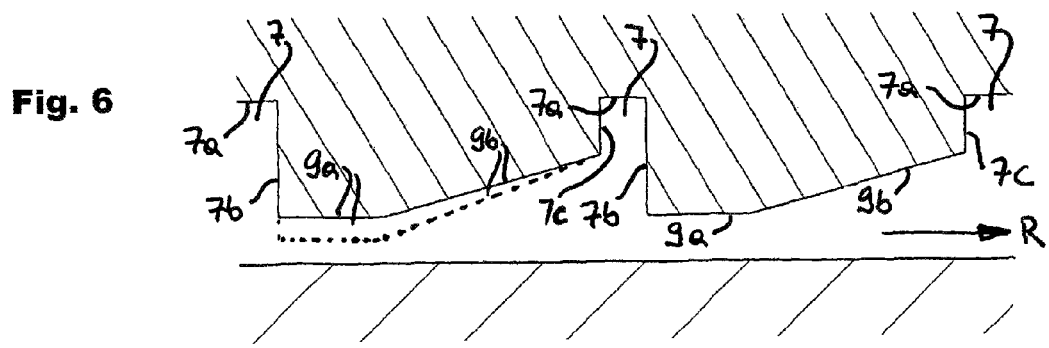
FIGS. 6 and 7 are views like FIG. 5 of other embodiments of the invention.

FIG. 6 shows another embodiment according to which the height of the plateau or first part 9a and the leading sidewall 7b of a groove as well as the slope of the second part 9b rises in direction toward the central passage 5. Also this is in accordance with FIG. 4.

Figure 7:
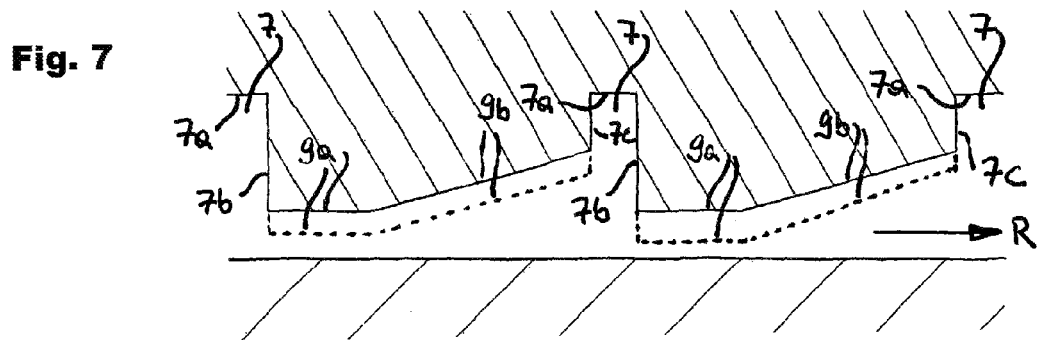

FIG. 7 shows in the left part, that toward the central passage 5, the height of both sidewalls 7b, 7c rises simultaneously by the same amount thus rising to the height of the second part 9b but maintaining its slope constant. According to the right part of FIG. 7 the trailing sidewall 7c rises less than the leading sidewall 7b thus rising again along the slope of the second part 9b toward the central passage. Also this corresponds to FIG. 4

As can be seen from FIGS. 5 to 7 different embodiments exist to provide the same result as shown in FIG. 4.

The invention claimed is:

1. An impeller of a centrifugal blood pump, comprising a discoidal body rotatable around an axis of rotation, the body comprising
 a) an upper surface;
 b) a lower surface;
 c) a central axially extending passage between the upper and lower surface for guiding blood axially through the body when the body is rotated in a pump chamber of a pump; and
 d) several blades supported by the upper surface for pumping blood when the body is rotated in the pump chamber of the centrifugal pump;
 e) several spiral grooves in the lower surface, each groove having a bottom and two sidewalls and being axially open, merging into an outer surface of the body and extending from this outer surface to the central passage for providing a pumping action of blood from the outer surface to the central passage when the body is rotated within the pump chamber;
 f) permanent magnets integrated in the body for driving the impeller by a magnetic field;
 wherein
 g) each groove also merges into the central passage;
 h) one of the sidewalls of each groove is a leading sidewall with respect to the regular direction of rotation and is higher above the bottom than the respective trailing sidewall;
 i) a respective surface area between each two neighboring grooves connects the leading sidewall and the trailing sidewall of the respective neighboring grooves, thus forming a tilted pad area between each pair of neighboring grooves;
 j) each surface area is subdivided angularly into a first part adjacent the leading sidewall of a respective groove forming a plateau in circumferential direction, and a second part extending between the plateau and the trailing sidewall of a respective neighboring groove and having a decreasing height toward the respective neighboring groove angularly; and
 k) at least one of the first and second parts forms a secondary incline along a spiral on the lower surface of the impeller body toward the axis.

2. The impeller according to claim 1, wherein in a circumferential direction the first part forms a plane plateau.

3. The impeller according to claim 1, wherein in a circumferential direction the second part is monotonically decreasing in height toward the respective neighboring groove until it merges into the lower trailing sidewall of the respective neighboring groove.

4. The impeller according to claim 1, wherein in a direction from the outer surface to the central passage, a free space between two neighboring grooves, and a free space between the lower surface and a pump housing is decreasing.

5. The impeller according to claim 1, wherein in a direction from the outer surface to the central passage, the height of the higher sidewall is constant and the height of the lower sidewall is increasing, by simultaneously maintaining the bottoms of two neighboring grooves within the same plane, thus providing the second part of the surface area between two grooves with a slope in a circumferential direction that is decreasing with decreasing distance to the central passage.

6. The impeller according to claim 1, wherein in a direction from the outer surface to the central passage, the height of the higher sidewall and thus the height of the plateau is increasing by simultaneously maintaining the bottoms of two neighboring grooves within the same plane.

7. The impeller according to claim 6, wherein in a direction from the outer surface to the central passage the height of the lower sidewall is increasing by the same gradient as the higher sidewall increases, thus providing the second part of each surface area between two grooves with an increasing height above the groove bottoms while and maintaining a constant slope in circumferential direction.

8. The impeller according to claim 6, wherein in a direction from the outer surface to the central passage the height of the lower sidewall is increasing by a smaller gradient than the higher sidewall or is constant thus providing the second part of the surface area between two grooves with a slope in circumferential direction that is increasing with decreasing distance to the central passage.

9. The impeller according to claim 1, wherein in a direction from the outer surface to the central passage a cross-section of each groove is decreasing.

10. A centrifugal blood pump comprising
a housing having an inlet port, an outlet port and a pump chamber connecting these ports and
an impeller located in the pump chamber including a body rotatable around an axis of rotation coaxial with the inlet port, the impeller having a central axial opening, communicating with the inlet port, several blades and free spaces between the blades, the free spaces being radially open and communicating with the central axial opening and with the outlet port via a volute surrounding the impeller;
a magnetic drive driving the impeller by a magnetic field interacting with permanent magnets integrated in the impeller; and
a hydrodynamic bearing formed by a plurality of spiral grooves in a lower surface of the impeller opposite an inner surface of a lower wall of the pump chamber, and
each groove having a bottom and two sidewalls and being axially open, merging into an outer surface of the body and extending from this outer surface to the central opening for providing a pumping action of blood from the outer surface to the central opening when the body is rotated within the pump chamber;
wherein
each groove also merges into the central opening;
one of the sidewalls of each groove is a leading sidewall with respect to the regular direction of rotation and is higher above the bottom than the respective trailing sidewall;
a respective surface area between each two neighboring grooves connects the leading sidewall and the trailing sidewall of the respective neighboring grooves, thus forming a tilted pad area between each pair of respective neighboring grooves;
each surface area is subdivided angularly into a first part adjacent the leading sidewall of a respective groove forming a plateau in circumferential direction and a second part extending between the plateau and the trailing sidewall of a respective neighboring groove and having a decreasing height toward the respective neighboring groove angularly; and
at least one of the first and second parts forms a secondary incline along a spiral on the lower surface of the impeller body toward the axis.

11. The impeller according to claim 10, wherein at least the second part has a height above the groove bottom that increases radially inward toward the axis.

* * * * *